(12) United States Patent
Sorensen

(10) Patent No.: US 9,482,216 B2
(45) Date of Patent: Nov. 1, 2016

(54) MULTIPLE SEGMENTED PERISTALTIC PUMP AND CASSETTE

(71) Applicant: Alcon Research, Ltd., Fort Worth, TX (US)

(72) Inventor: Gary P. Sorensen, Laguna Niguel, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 0 days.

(21) Appl. No.: 14/302,636

(22) Filed: Jun. 12, 2014

(65) Prior Publication Data

US 2014/0328697 A1  Nov. 6, 2014

Related U.S. Application Data

(63) Continuation of application No. 12/755,539, filed on Apr. 7, 2010, now Pat. No. 8,790,096.

(60) Provisional application No. 61/175,975, filed on May 6, 2009.

(51) Int. Cl.
| | |
|---|---|
| *F04B 43/02* | (2006.01) |
| *A61M 1/00* | (2006.01) |
| *A61M 5/142* | (2006.01) |
| *F04B 43/12* | (2006.01) |

(52) U.S. Cl.
CPC .......... *F04B 43/025* (2013.01); *A61M 1/0058* (2013.01); *A61M 1/0072* (2014.02); *A61M 5/14232* (2013.01); *F04B 43/1253* (2013.01); *F04B 43/1269* (2013.01); *A61M 2205/12* (2013.01); *A61M 2206/22* (2013.01)

(58) Field of Classification Search
CPC .... A61M 1/1039; A61M 1/28; A61M 1/284; A61M 5/14228; A61M 4/14232; F04B 43/12; F04B 43/1253; F04B 43/1261; F04B 43/1269; F04B 43/1292
USPC ...... 417/474, 475, 476, 477.1, 477.2, 477.5, 417/477.7
See application file for complete search history.

(56) References Cited

U.S. PATENT DOCUMENTS

| | | | | |
|---|---|---|---|---|
| 7,238,164 | B2* | 7/2007 | Childers et al. | ............. 604/6.11 |
| 7,645,127 | B2* | 1/2010 | Hagen | ................ F04B 43/1253 |
| | | | | 417/477.1 |
| 2006/0245964 | A1 | 11/2006 | Koslov | |
| 2009/0053084 | A1* | 2/2009 | Klein | ........................ 417/477.1 |

FOREIGN PATENT DOCUMENTS

RU    2197277 C2    1/2003

* cited by examiner

*Primary Examiner* — Patrick Hamo

(57) ABSTRACT

In various embodiments, a surgical cassette, configured to engage peristaltic pump rollers, may include two or more pump segments between a sheet and a substrate coupled to the sheet. The two or more pump segments on the cassette may produce additional flow (e.g., approximately twice the flow for two segments as opposed to one) than if the cassette had only one pump segment engaging the roller. Further, in some embodiments, the two or more pump segments and rollers on the roller head may be configured to provide a flow profile in which a peak of a pulse from a first pump segment is at least partially out of phase with a peak of a pulse from the second pump segment. The combined resultant flow may then have a flow profile with pulsation amplitudes that are smaller than the individual pump segment pulsation amplitudes.

20 Claims, 14 Drawing Sheets

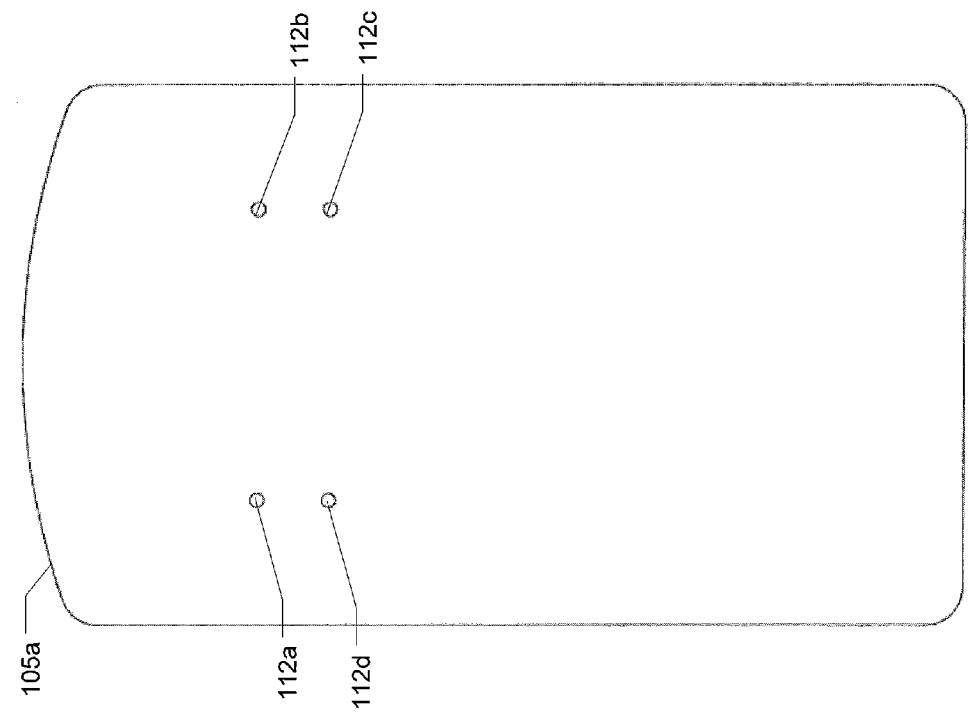
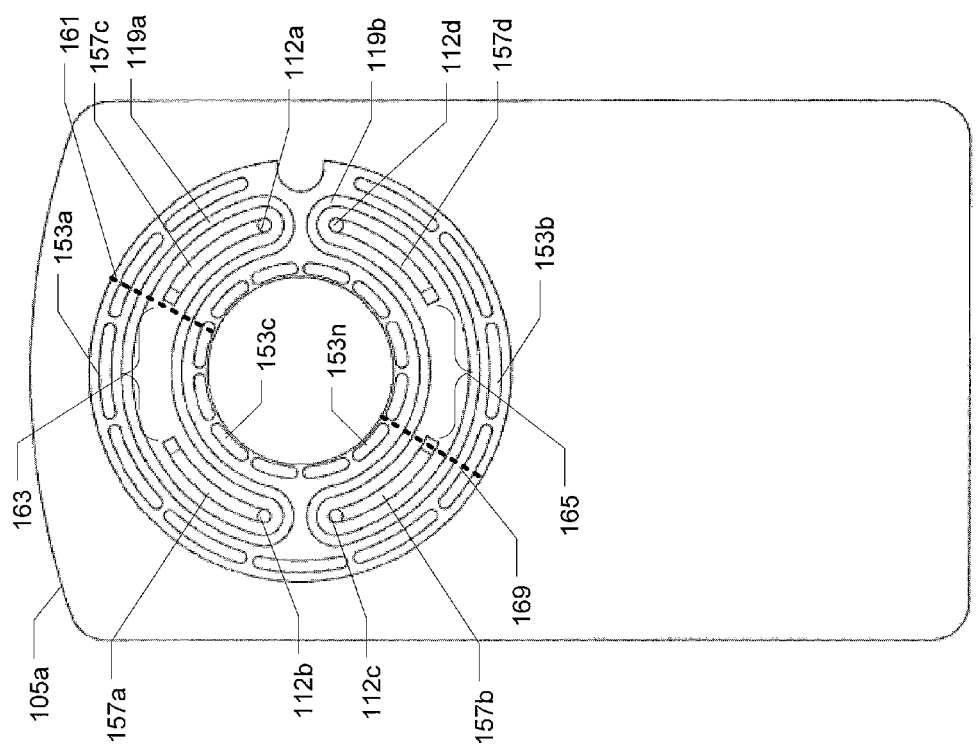

MULTIPLE SEGMENTED PERISTALTIC PUMP AND CASSETTE

PRIORITY CLAIM

This application:

(a) is a continuation application of U.S. patent application Ser. No. 12/755,539 titled "MULTIPLE SEGMENTED PERISTALTIC PUMP AND CASSETTE" which was filed Apr. 7, 2010, whose inventor is Gary P. Sorensen which is hereby incorporated by reference in its entirety as though fully and completely set forth herein, and (b) claims the benefit of priority of U.S. Provisional Application Ser. No. 61/175,975 (U.S. patent application Ser. No. 12/755,539 claimed the benefit of priority of provisional application Ser. No. 61/175,975 titled "MULTIPLE SEGMENTED PERISTALTIC PUMP AND CASSETTE" filed on May 6, 2009, whose inventor is Gary P. Sorensen), which is also hereby incorporated by reference in its entirety as though fully and completely set forth herein.

FIELD OF THE INVENTION

The present invention generally pertains to pumps. More particularly, but not by way of limitation, the present invention pertains to peristaltic pumps.

DESCRIPTION OF THE RELATED ART

Peristaltic pumps may be used in many different applications including delivery of fluid during surgical applications (e.g., ophthalmic surgical applications). Peristaltic pumps may operate by compressing a length of tubing to move a fluid in the tubing or squeeze a molded flow channel between an elastomeric sheet and a rigid substrate to move a fluid between the elastomeric sheet and the rigid substrate. Rotating roller heads applied against the tubing or elastomeric sheet may be used for compressing the tubing or elastomeric sheet. While peristaltic pumps may provide predictable flow properties, they may also impart unwanted flow and pressure pulsations.

SUMMARY OF THE INVENTION

In various embodiments, a surgical cassette, configured to engage peristaltic pump rollers, may include two or more pump segments between a sheet and a substrate coupled to the sheet. In some embodiments, a roller head with multiple rollers may be configured to engage the two or more pump segments to provide a flow of fluid through the pump segments. In some embodiments, the inlet ports of the pump segments may pull fluid from a common source and the exit ports of the pump segments may push fluid to a common exhaust. The pump segments may be arranged in a circle to correspond with a circular configuration of rollers on the roller head (other shapes are also contemplated). The two or more pump segments on the cassette may produce additional flow (e.g., approximately twice the flow for two segments as opposed to one) than if the cassette had only one pump segment engaging the roller.

Further, in some embodiments, the two or more pump segments and rollers on the roller head may be configured to provide a flow profile with pulses that are at least partially out of phase with each other (e.g., peaks of the pulses from each pump segment are not aligned) when the pump segments are engaged by the roller head. For example, the pump segments may include a first pump segment and a second pump segment arranged such that a peak of a pulse in the flow profile provided from the first pump segment is approximately 180 degrees out of phase with a peak of a pulse in the flow profile provided by the second pump segment (e.g., the peak of the first pump segment pulse may align with a valley of the second pump segment pulse). In some embodiments the combined resultant flow (which may be twice the flow of each separate pumping channel) may have a flow profile with pulsation amplitudes that are smaller than pulsation amplitudes of pulses in the individual flow profiles of the first pump segment and second pump segment.

BRIEF DESCRIPTION OF THE DRAWINGS

For a more complete understanding of the present invention, reference is made to the following description taken in conjunction with the accompanying drawings in which:

FIG. 1c illustrates a front view of a substrate for two pump segments, according to an embodiment;

FIG. 1d illustrates a back view of the substrate for two pump segments, according to an embodiment;

It is to be understood that both the foregoing general description and the following detailed description are exemplary and explanatory only and are intended to provide a further explanation of the present invention as claimed.

DETAILED DESCRIPTION OF THE EMBODIMENTS

Incorporation by Reference

U.S. Pat. No. 6,293,926 entitled "Peristaltic Pump and Cassette," by Gary P. Sorensen and Tamer Akkas, filed Nov. 10, 1999 is hereby incorporated by reference in its entirety as though fully and completely set forth herein.

U.S. Pat. No. 6,572,349 entitled "Peristaltic Pump and Cassette," by Gary P. Sorensen and Tamer Akkas, filed May 1, 2001 is hereby incorporated by reference in its entirety as though fully and completely set forth herein.

Figure 1B:
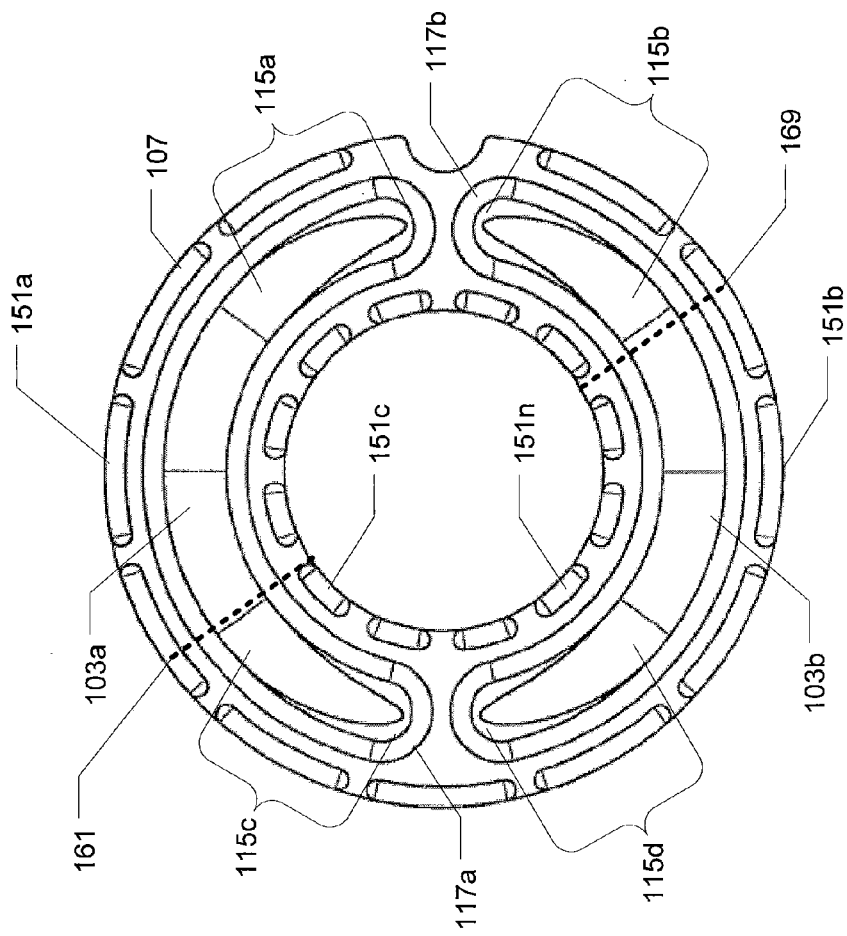
FIG. 1b illustrates a back view of the elastomeric sheet with two pump segments, according to an embodiment.
Figure 1A:
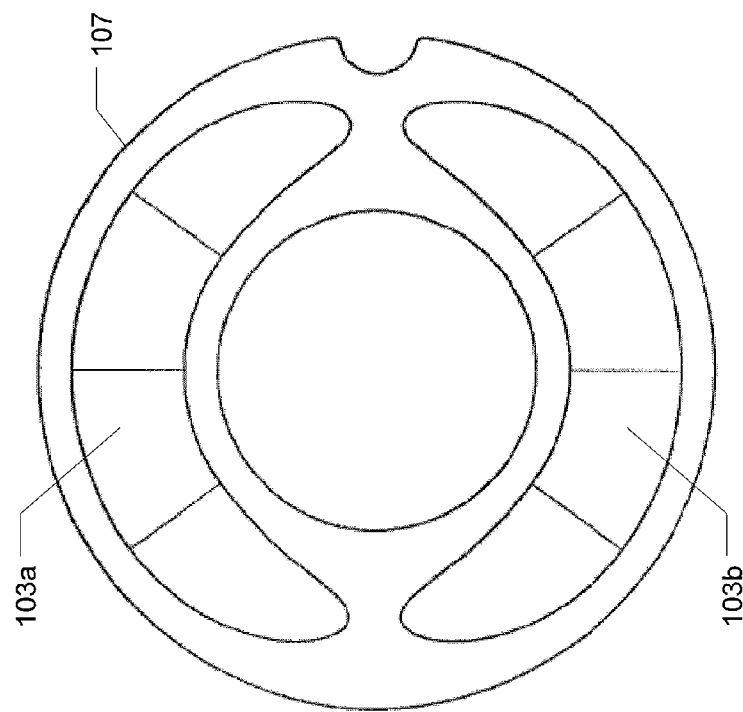
FIG. 1a illustrates a front view of an elastomeric sheet with two pump segments, according to an embodiment.
Figure 2A:
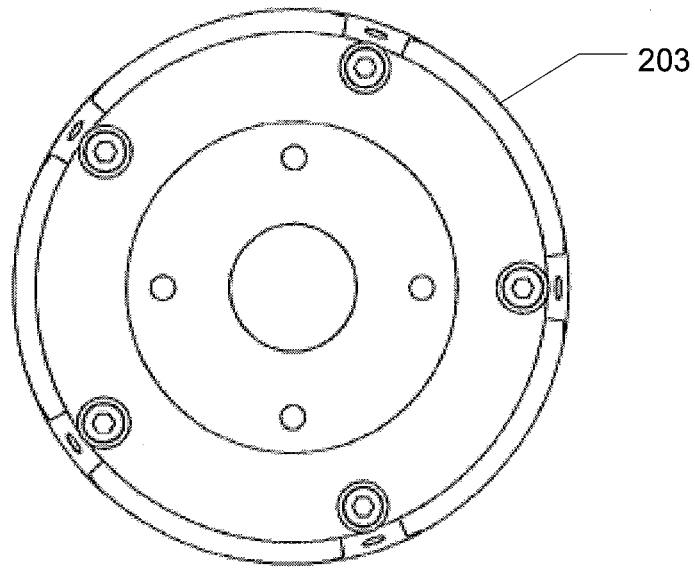
FIG. 2a illustrates a top view of a roller head, according to an embodiment.
Figure 2B:
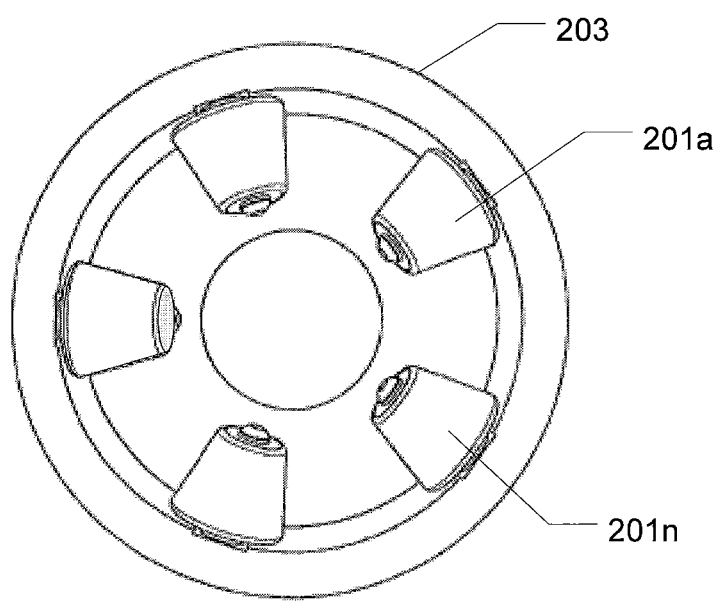
FIG. 2b illustrates a bottom view of the roller head, according to an embodiment.
Figure 5B:
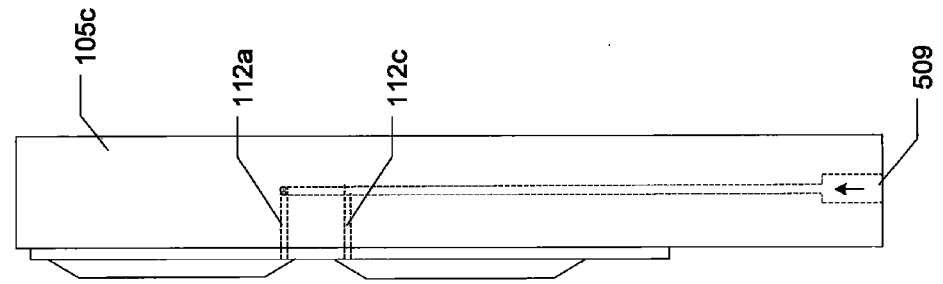
FIGS. 5a-c illustrates an alternate embodiment of a cassette with additional cassette structures engaging a roller head with additional rollers.
Figure 5A:
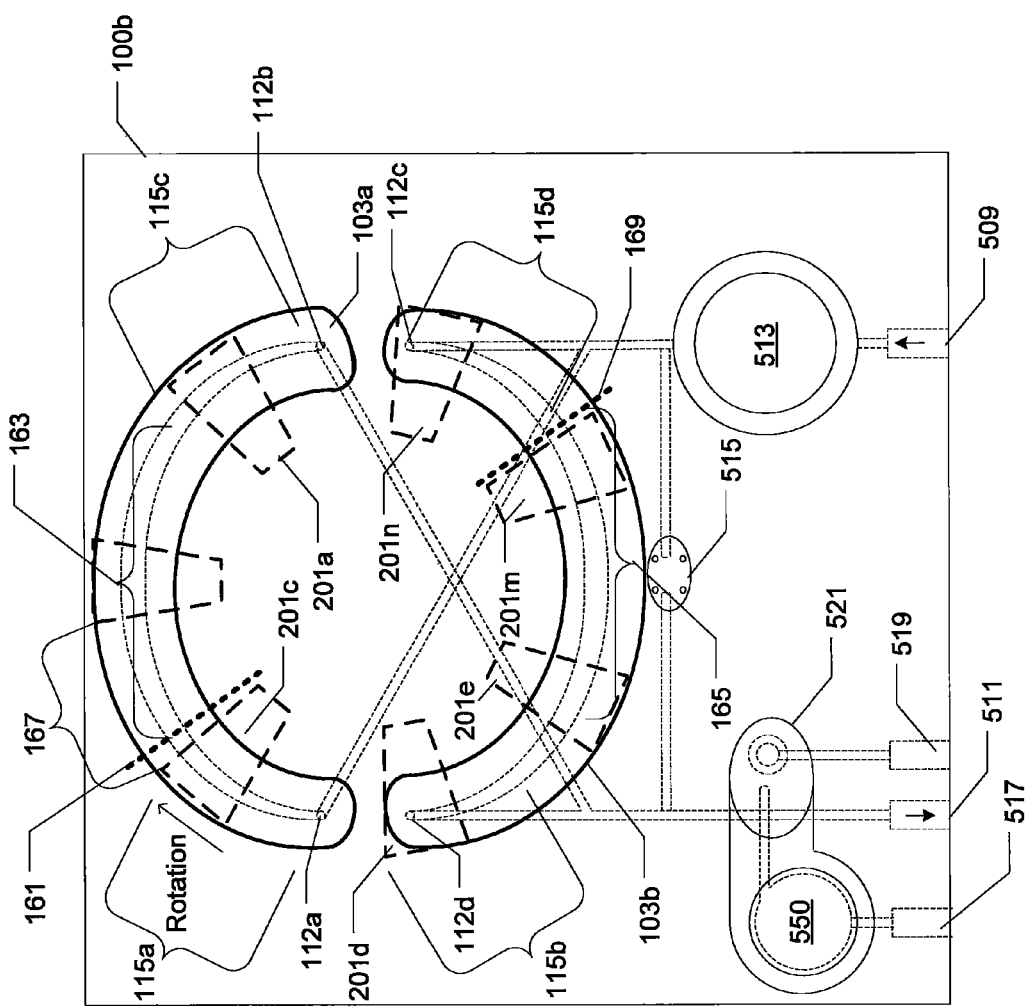
Figure 7:
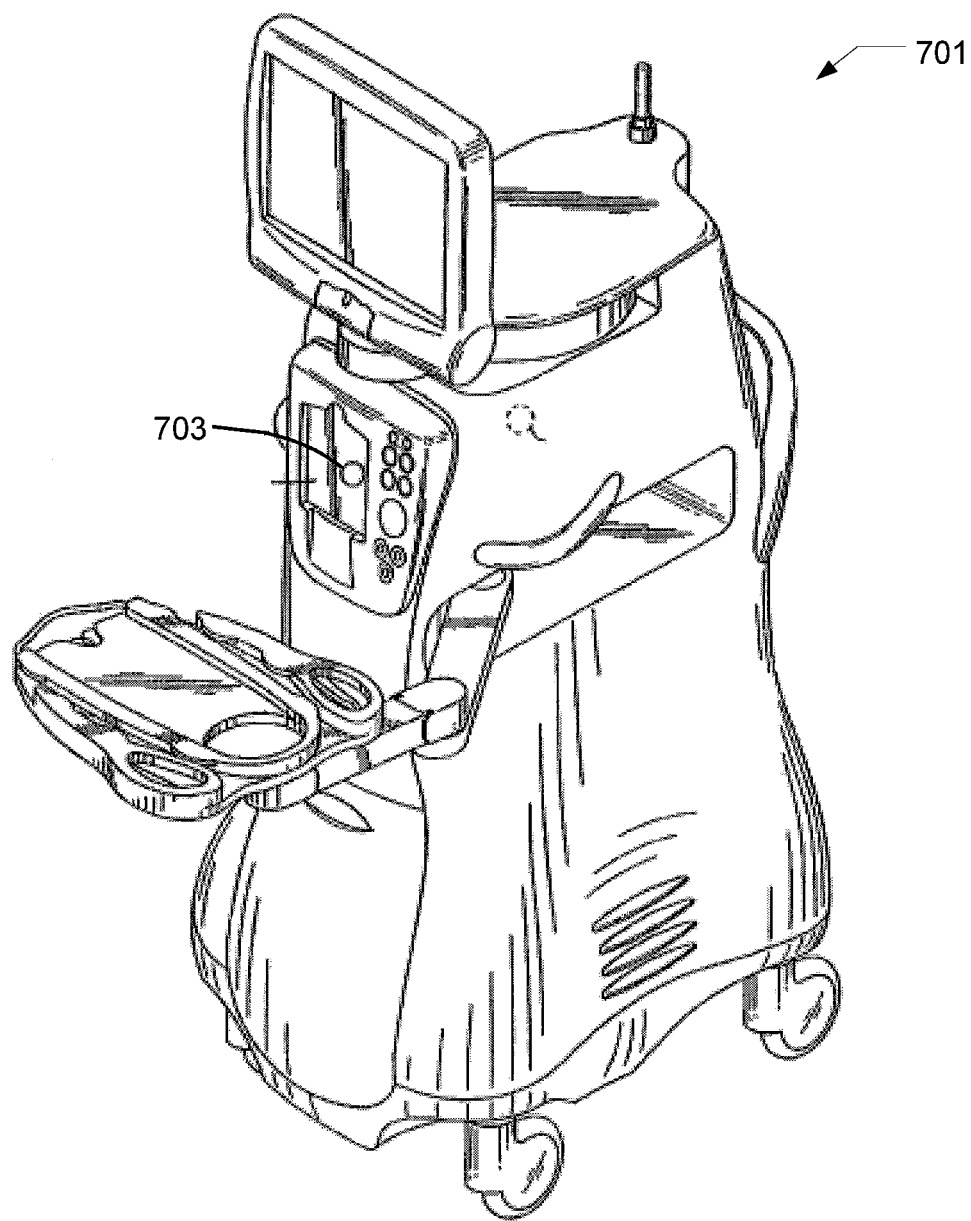
FIG. 7 illustrates an embodiment of a console for using a cassette with multiple pump segments.

FIGS. 1a-b illustrate a sheet 107 (such as an elastomeric sheet) for coupling to a substrate 105 (e.g., any of substrates 105a-c—generally referred to herein as substrate 105) to define two or more pump segments (e.g., any of pump segments 103a-b—generally referred to herein as pump segments 103) in a cassette 100 (e.g., any of cassettes 100a-b—generally referred to herein as cassette 100). Cassette 100 may use pump segments 103 to provide aspiration and/or infusion of fluid 155 (e.g., see FIG. 5c) for a surgical console (e.g., an ophthalmic surgical console 701 as seen in FIG. 7). FIGS. 1c-d illustrate an embodiment of substrate 105a (other embodiments of the substrate 105 are also contemplated). In various embodiments, the two or more pump segments 103 may be formed between the sheet 107 and the substrate 105 of the cassette 100. Sheet 107 may be made of a flexible, moldable material such as silicone rubber or thermoplastic elastomer. Other materials are also contemplated. Substrate 105 may be made of a material that is rigid with respect to sheet 107, such as a rigid thermoplastic, and may be made by any suitable method, such as machining or injection molding. In some embodiments, the sheet 107 may be bonded or mechanically attached to the substrate 105 (e.g., through adhesive, heat fusion, mechanical crimping, rivets, etc). In some embodiments, protrusions 151a-n on an outer perimeter and/or interior of sheet 107 may engage corresponding recesses 153a-n on substrate 105 to connect the sheet 107 to the substrate 105 and help prevent rotation of the sheet 107 when acted upon by rollers (e.g., see rollers 201a-n in FIG. 2b) (rollers 201a-n—generally referred to herein as rollers 201). As used herein, the label "a-n" is used to refer to the various elements in the presented embodiments for that element. For example, "rollers 201a-n" is used to refer to the rollers shown in, for example, FIG. 2b (FIG. 2b shows 5 rollers) and FIG. 5a (FIG. 5a shows 7 rollers) (two rollers in FIG. 2b are labeled 201a and 201n and two rollers in FIG. 5a are labeled 201a and 201n although some of the rollers in each of these FIGs. may not have specific labels). In some embodiments, protrusions 117a,b (which may outline the respective pump segments 103) may fit into corresponding recesses 119a,b (see FIG. 3a). Protrusions 117a,b (and/or 151a-n) may be secured to respective recesses 119a,b (and/or 153a-n) to retain the sheet 107 to the substrate 105. In some embodiments, protrusions 117a,b (and/or 151a-n) may be secured to respective recesses 119a,b (and/or 153a-n) through a mechanical/friction fit, adhesive, heat fusion, etc. In some embodiments, protrusions 117a,b may be secured to respective recesses 119a,b to form a seal to prevent escape of a pump fluid 155 (such as BSS™ (balanced salt solution)) from the pump segments 103.

Figure 3A:
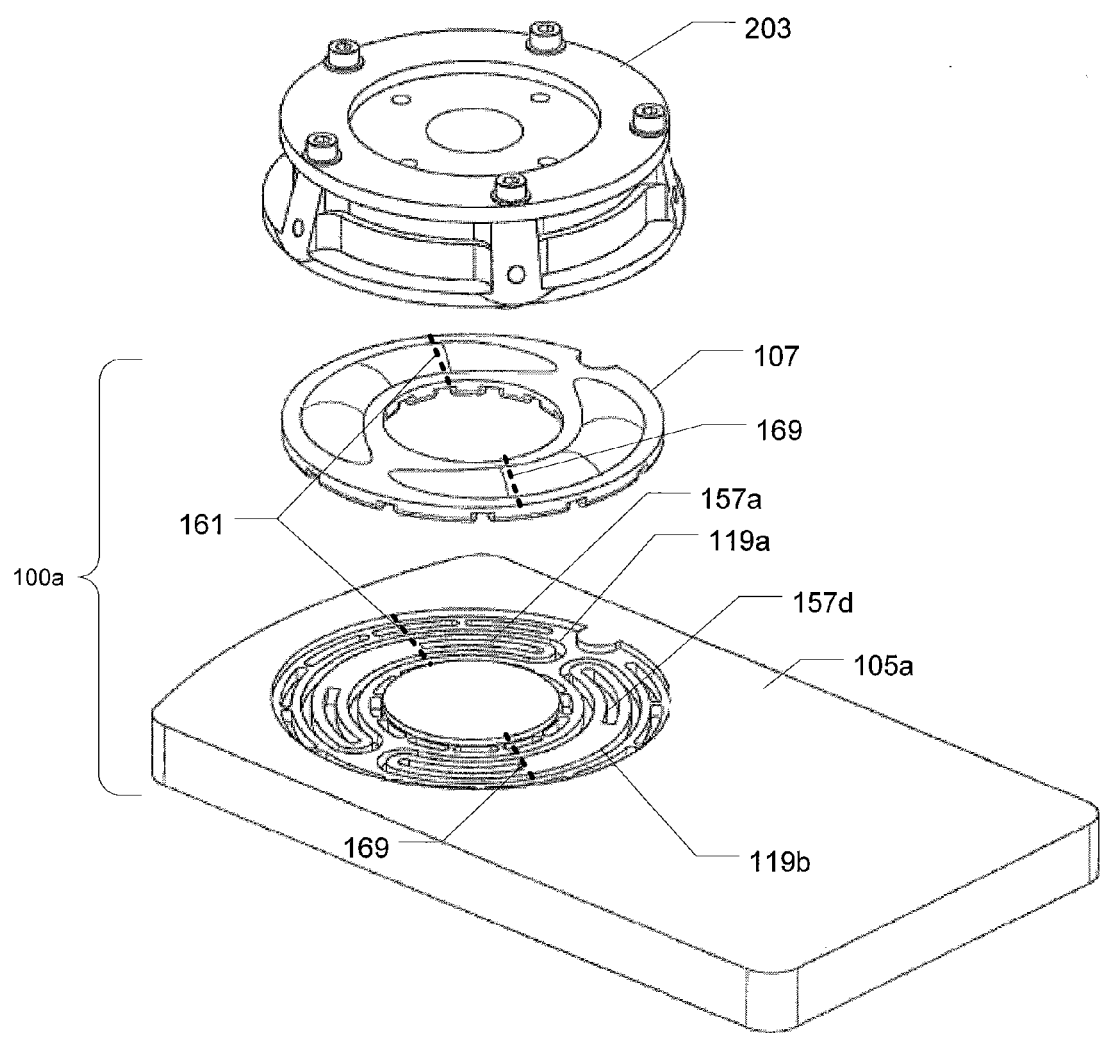
FIGS. 3a-b illustrate isometric views of an expanded cassette assembly view, according to an embodiment.
Figure 3B:
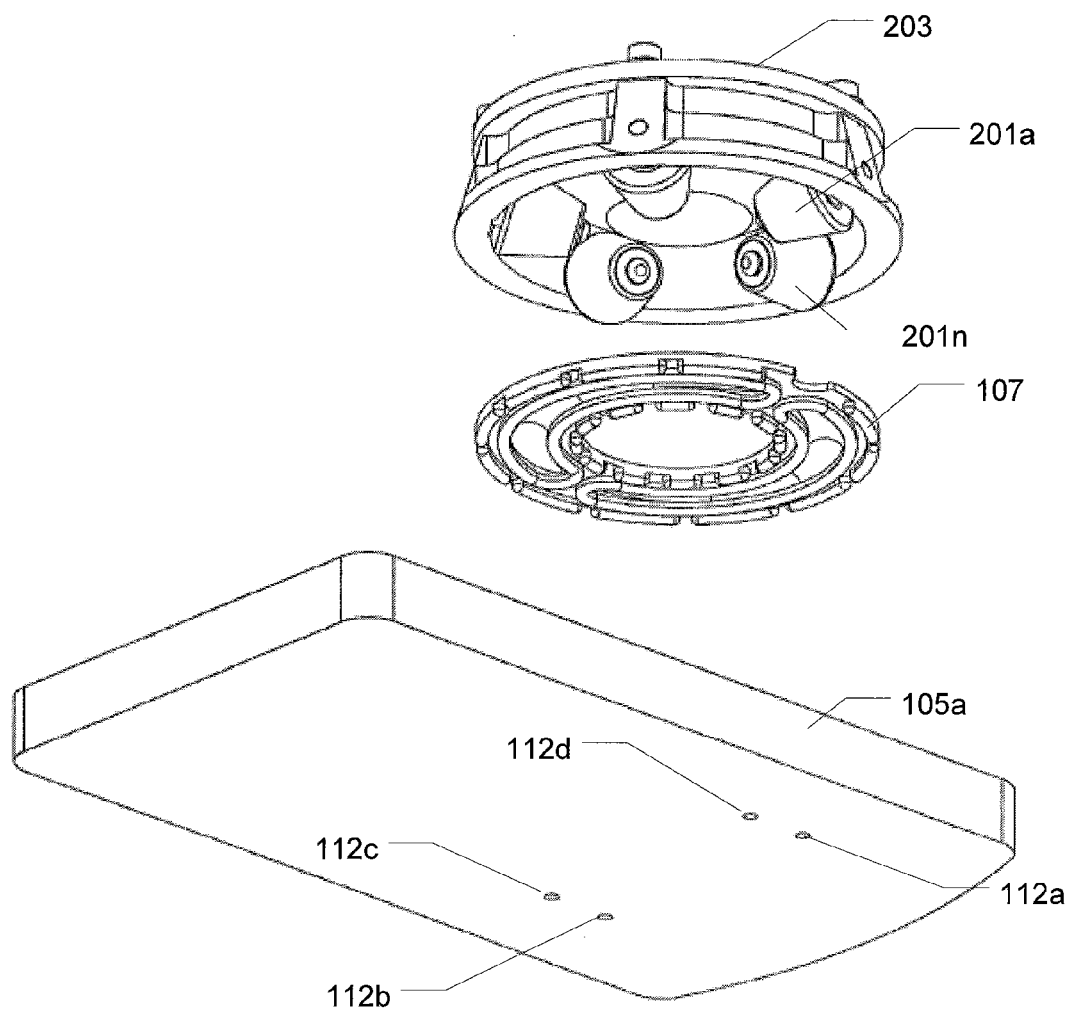
Figure 3C:
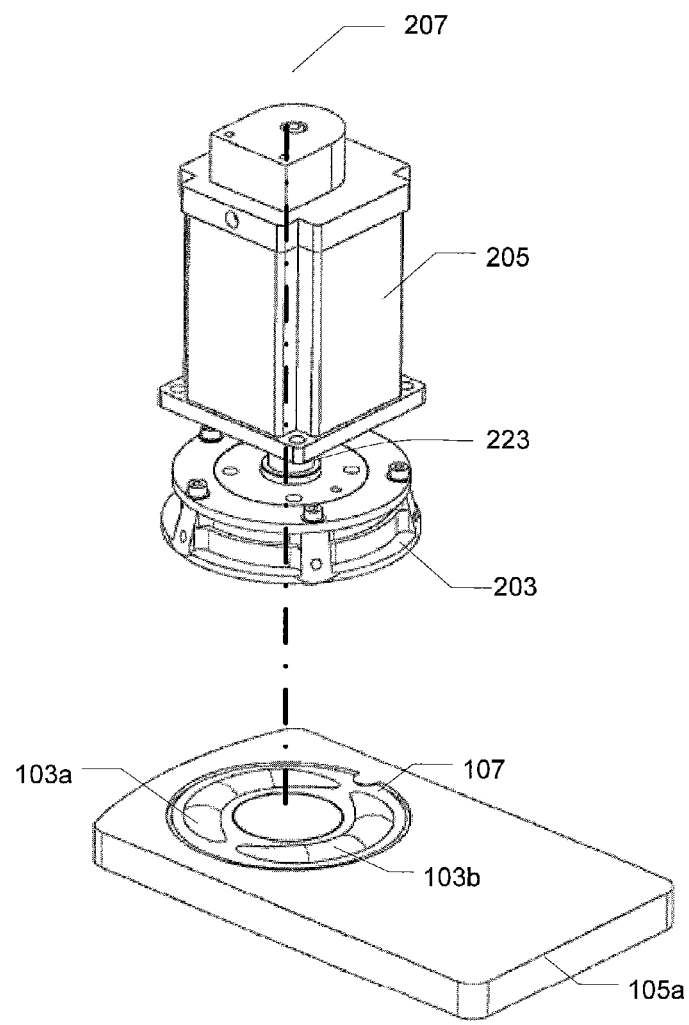
FIG. 3c illustrates a side view of the roller head and motor, according to an embodiment.
Figure 3D:
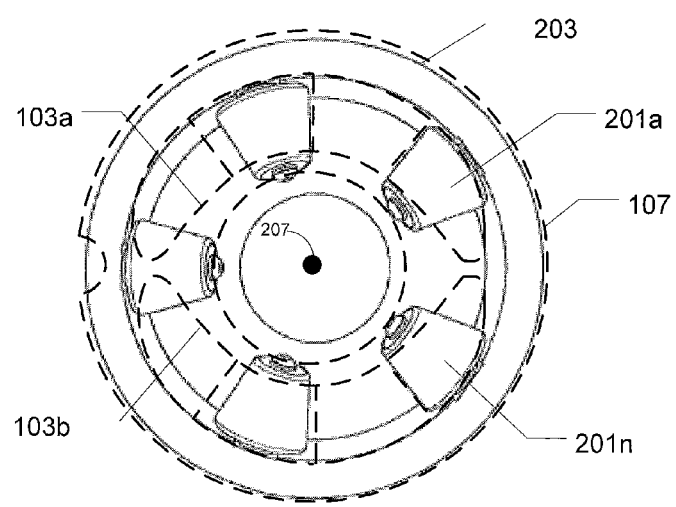
FIG. 3d illustrates an outline of the roller head engaging the sheet, according to an embodiment.

In various embodiments, fluid 155 may be pumped through the cassette 100 when a series of rollers 201 engage the two or more pump segments 103 on the cassette 100. FIGS. 2a-b illustrate a roller head 203 with rollers 201. FIGS. 3a-b illustrate isometric views of an embodiment of an expanded cassette assembly view showing the rollers 201, the sheet 107, and the substrate 105. FIG. 3c illustrates an embodiment of the roller head 203 and corresponding peristaltic pump motor 205. In some embodiments, the rollers 201 on the roller head 203 may be radially mounted from an axis of rotation 207 of the peristaltic pump motor 205 (e.g., a stepper or direct current (DC) servo motor, or other motor (such as an alternating current (AC) motor)) and may be configured to compress the pump segments 103 against the underlying substrate 105. The rollers 201 may be mounted to pump motor 205 through roller head 203 and shaft 223 such that pump motor 205 may rotate roller head 203 in a plane generally normal or perpendicular to axis 207 of shaft 223 (see also solid circle 207 in FIG. 3d showing where the axis 207 is perpendicular to the plane of the rollers 201), and the longitudinal axes of rollers 201 may be generally radial to the axis of shaft 223. FIG. 3d illustrates an embodiment of the rollers 201 engaging two pump segments 103a,b on sheet 107 (indicated in dashed lines). The two or more pump segments 103 on the cassette 100 may produce additional flow (e.g., approximately twice the flow for two segments as opposed to one) than if the cassette 100 had only one pump segment engaging the roller head 203.

Figure 4A:
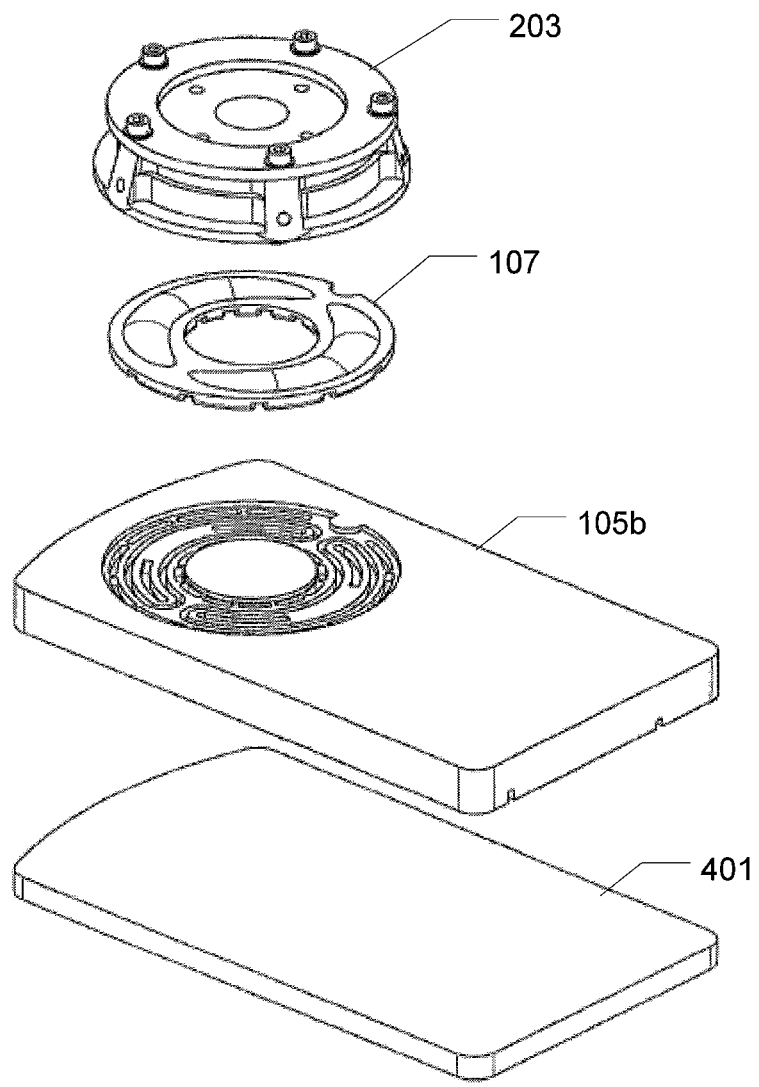
FIGS. 4a-b illustrate isometric views of an expanded cassette assembly view, according to another embodiment.
Figure 4B:
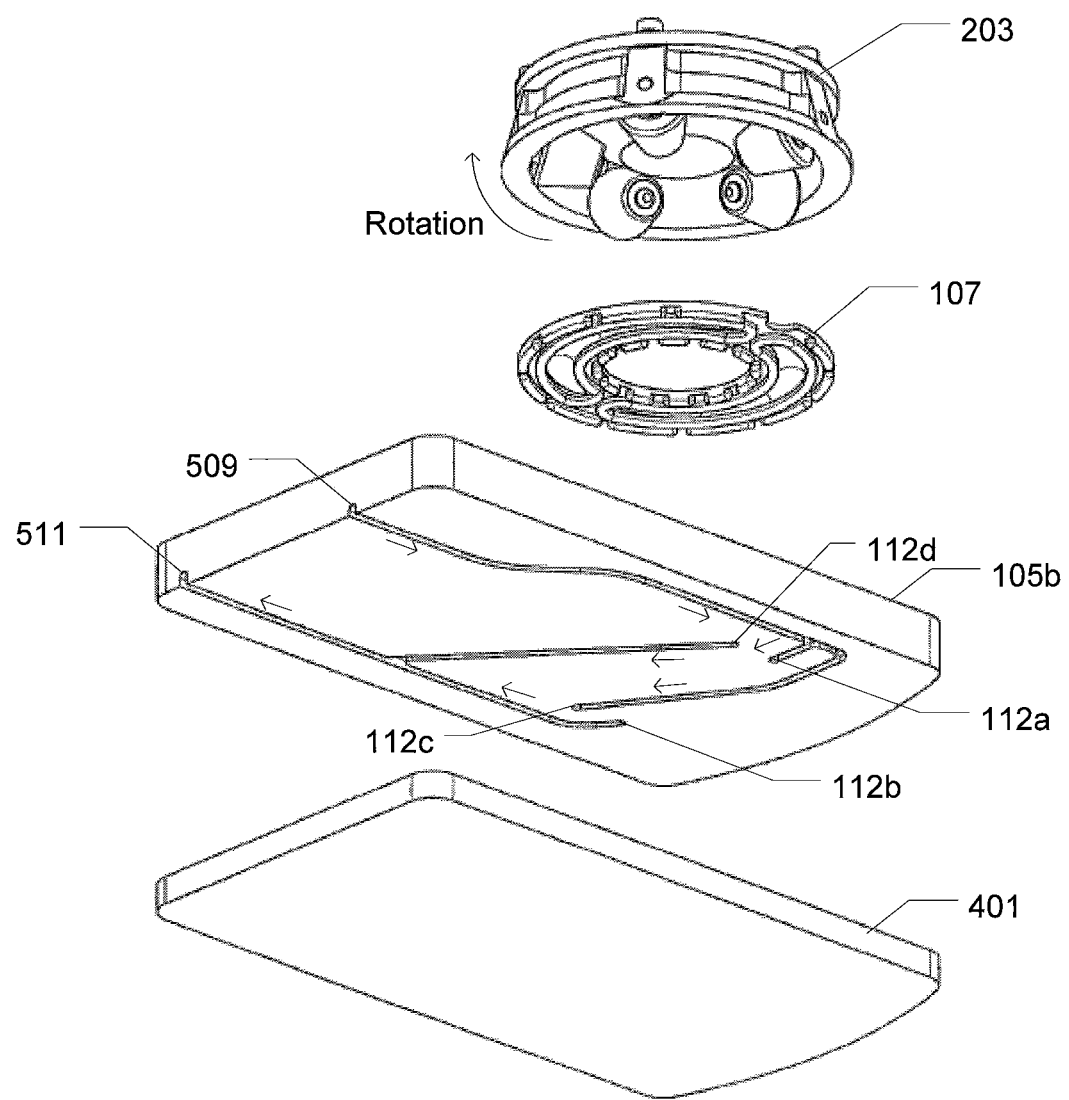
Figure 5C:
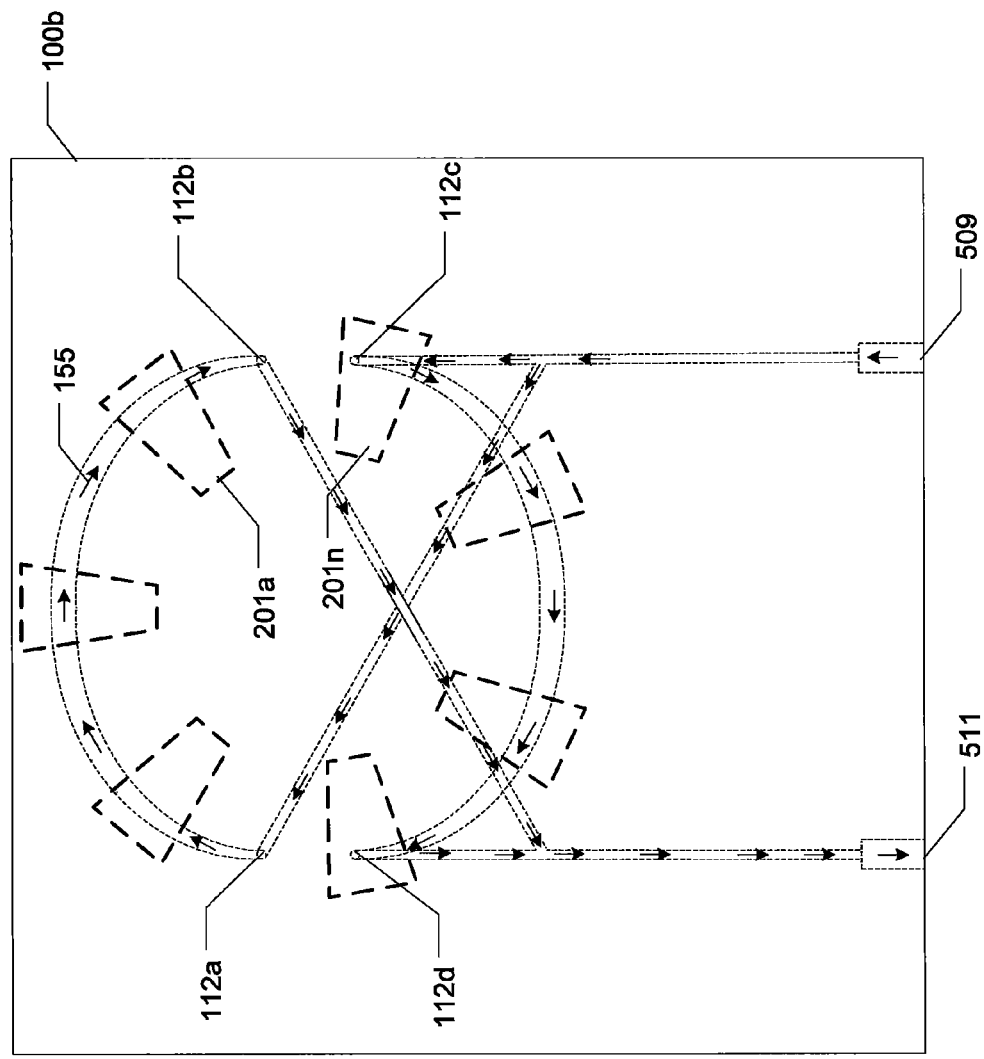

In some embodiments, pump segments 103 may be generally planar, arcuate in shape (within the plane), and have a radius approximating that of rollers 201 about shaft 223. Pump segments 103 may fluidly connect ports in the substrate 105 (e.g., ports 112a-d—generally referred to herein as ports 112). The ports 112 may provide respective inlets and outlets for fluid 155 being pumped through the pump segments 103. As seen, for example, in the embodiments of FIGS. 4a-b and FIGS. 5a-c, various ports 112 may be fluidly coupled to the pump segments 103 and to each other to pull fluid 155 from a common source (e.g., inlet 509) and provide a combined resultant flow to, for example, outlet 511. FIGS. 4a-b illustrate fluid flow for rollers 201 rotating counterclockwise relative to the sheet 107 and FIGS. 5a-c illustrate fluid flow for rollers 201 rotating clockwise relative to the sheet 107. FIGS. 4a-b and FIGS. 5a-c also show different flow path embodiments for flow between ports 509 and 511 (which result in ports 112a-d being on opposite sides of the substrate 105 in these respective embodiments). As seen in FIG. 4a-b, an additional substrate portion 401 may be sealed over substrate 105 (e.g., using adhesive, heat fusion, etc.) to enclose one or more of the fluid paths formed in substrate 105.

Figure 9:
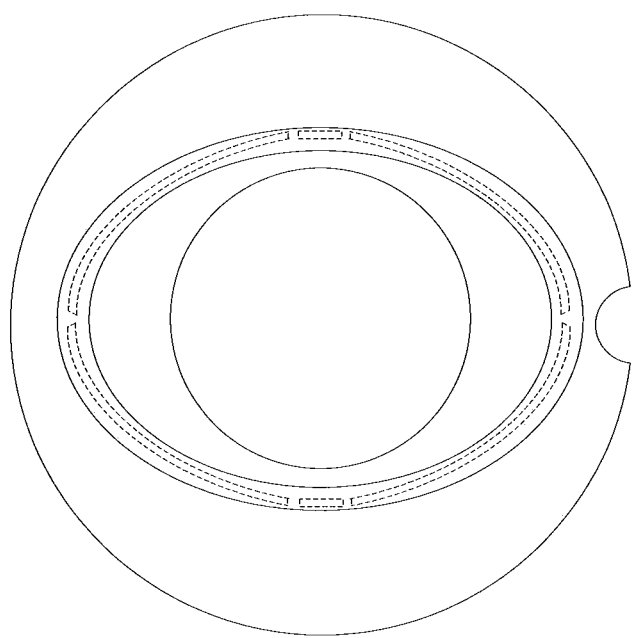
FIG. 9 illustrates an embodiment of a sheet with an elliptical shape.

In some embodiments, a single sheet 107 may include two or more pump segments 103. While multiple sheets with separate pump segments are also contemplated, forming the two or more pump segments 103 in a single sheet 107 may reduce the number of components and allow assembly of the pump segments 103 in fewer manufacturing operations (which may reduce cost relative to an implementation with multiple separate pump segments). In some embodiments, separate sheets may be used for one or more of the pump segments 103 and the sheets may be arranged to correspond with a configuration of the rollers 201 (e.g., in a circle if the rollers 201 are arranged in a circle). While embodiments are shown for circular roller configurations and pump segments 103, other shapes/configurations are also contemplated. For example, FIG. 9 illustrates an embodiment with elliptical pump segments. In various embodiments, rollers on a peristaltic pump roller head may be arranged to engage the various pump segment patterns to force flow through the various pump segments.

In some embodiments, cassette 100 may be received into cassette receiving portion 703 of surgical console 701 (e.g., see FIG. 7) and may be held in close proximity to rollers 201 such that rollers 201 compress portions of pump segments 103 (by pressing the sheet 107 against substrate 105) as roller head 203 rotates. The longitudinal axes of the rollers 201 may be arranged so that rollers 201 may contact pump segments 103 generally parallel with the plane of pump segments 103. Rollers 201 may be tapered along their axial length to accommodate the difference in path length traveled by the inner and outer sections of rollers 201 as roller head 203 rotates. As the rollers 201 rotate, a bolus (e.g., bolus 167) of fluid 155 may be moved between adjacent rollers. As the rollers 201 roll over and away from an inlet port (e.g., inlet ports 112a,c), a corresponding fluid bolus may be pulled into the pump segment 103 through the inlet port (because of a vacuum created by the roller pushing fluid 155 away from the inlet). As the rollers 201 approach and roll over an exit port, a corresponding fluid bolus may travel through the exit port (e.g., see exit ports 112b and 112d in FIG. 5a).

In various embodiments, the two (or more) active pump segments 103 in the sheet 107 may be acted upon by a single hub roller assembly (e.g., including rollers 201 and roller head 203). As rollers 201 engage the pump segments 103, each roller may first roll over a transition region (e.g., transition regions 115a-d—generally referred to herein as transition region 115) with an underlying transition channel (e.g., transition channels 157a-d—generally referred to herein as transition channel 157). In some embodiments, the sheet 107 may not include transition regions 115 and the substrate 105 may not include transition channels 157. As the rollers 201 roll off of the transition region 115 (and correspondingly, off of the transition channel 157), the rollers 201 may form an internal seal within the pump segment 103 (e.g., at point 161 indicated with dashed lines on pump segment 103a and at point 169 on pump segment 103b) by pressing the sheet 107 fully against substrate 105 at the seal point (in the absence of transition regions and transition channels, the roller 201 may form a seal at the start of the roller's engagement with the sheet 107). The internal seal may move as the roller (e.g., roller 201c in FIG. 5a) rolls through the "active" region 163 (or, for example, roller 201m in FIG. 5a rolls through active region 165 on the lower pump segment 103b). As the roller moves, fluid 155 in front of the roller's motion may be pushed through the pump segment 103 resulting in fluid 155 behind the roller's motion being pulled from the inlet (e.g., inlet 112a). As the next roller (e.g., roller 201d in FIG. 5a) on the roller head 203 approaches the transition region 115/transition channel 157 behind the roller that is currently forming an internal seal, the next roller may begin to reduce the cross sectional space between the sheet 107 underlying the non-sealed roller and the substrate 105. Because of the geometry of the transition region 115 and the underlying transition channel 157, the non-sealed roller on the transition region 115 may have fluid 155 under the roller (e.g., in the transition channel 157) preventing a seal. As the cross sectional space is reduced (e.g., as the non-sealed roller approaches the seal point or start of the active region), fluid 155 being pulled by the sealed roller may slowly be constrained. The fluid flow from the inlet as a result of the sealed active roller may slowly be reduced by the transition roller until the transition roller forms a new seal at the seal point 161 (or 169) and becomes the new active roller (which may effectively isolate the previous sealed roller). The sequence may then be repeated as the next roller on the roller head 203 engages the start of the transition region 115/transition channel 157.

Figure 6:
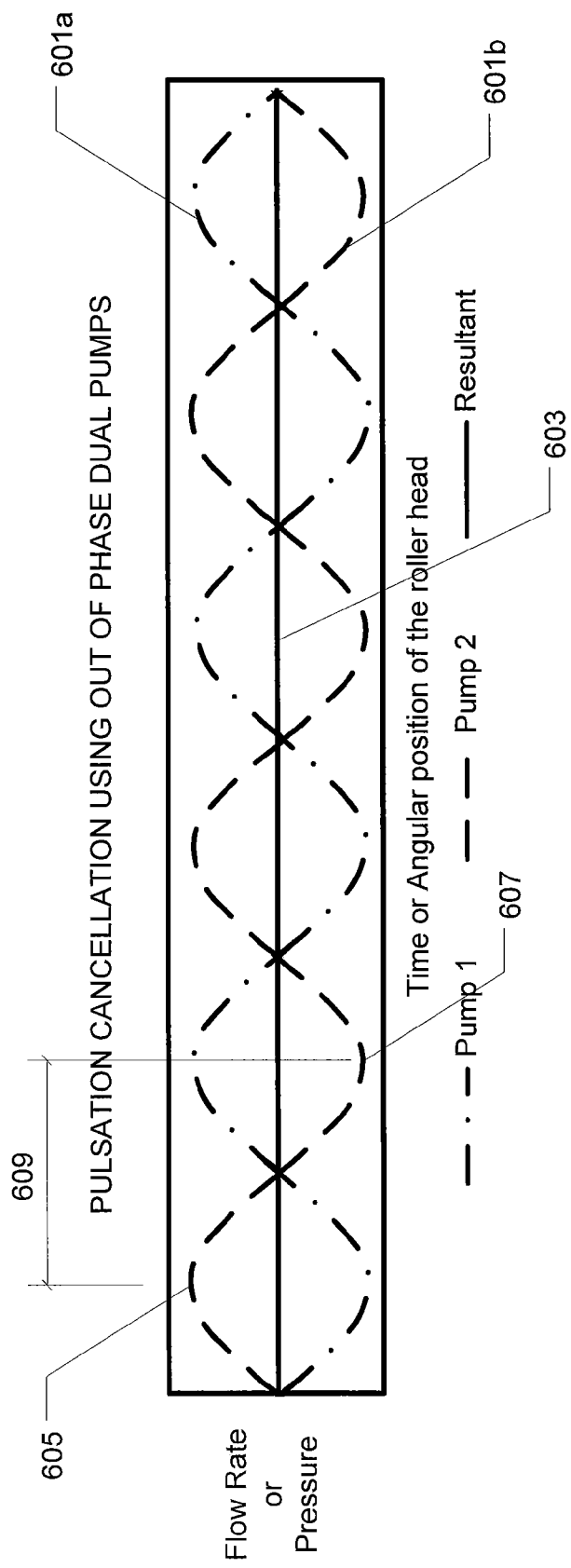
FIG. 6 illustrates a chart of individual pump flow profiles and a combined resultant flow profile, according to an embodiment.

The sequence of rollers 201 engaging the transition region 115 and then forming a moving internal seal (with a subsequent roller slowly reducing fluid flow until the subsequent roller forms a seal) may result in cyclical variations (or "pulses") in the fluid flow/pressure profiles of fluid 155 being pulled from the inlet (e.g., inlet 112a) and/or being pushed to the exhaust (e.g., exhaust 112b). The cassette 100 may include two or more pump segments 103 that may also be pulling fluid 155 from the same inlet and/or pushing fluid 155 to the same outlet (e.g., inlet 112a and inlet 112c may be fluidly coupled to the same aspiration line through port 509 and therefore be pulling fluid 155 from the same source). The positioning of the rollers 201 may be used to create offsetting pulses such that a pulse peak created in the fluid flow profile from inlet 112a may be offset by a corresponding pulse valley in the fluid flow profile from inlet 112c resulting in a more constant fluid flow/pressure profile from the source to inlet 112a and 112c. The flow profile (e.g., as seen in FIG. 6) may be representative of the flow rate of the fluid 155 or the pressure of the fluid 155 over time (or angular position of the roller head 203 which may be dependent upon time). Similarly, fluid flow in the pump segments 103 to exhaust 112b and 112d (which may both lead to a common exhaust port 511 on the cassette) may have offsetting pulses in their respective flow profiles resulting in a more constant resultant fluid flow/pressure to the common exhaust.

The pump segments 103 may be angularly spaced relative to the rollers 201 such that pulsations in the flow profile produced by the action of the rollers 201 on one segment (e.g., segment 103a) may be out of phase with pulsations in the flow profile produced by the other segment (e.g., segment 103b). For example, pulses in the flow profile provided through the pump segment 103a may be approximately 180 degrees out of phase with the pulses in the flow profile provided by pump segment 103b such that a peak of a pulse from pump segment 103a may be 180 degrees out of phase with a peak of a pulse from pump segment 103b (in other words, the peak of the pulse from pump segment 103a may be in phase with a valley of the pulse from pump segment 103b). In some embodiments, the pulses in the flow profiles may be out of phase by more or less than 180 degrees. For example, if more than two pump segments are used, the pulses may be arranged to be out of phase by an amount calculated to reduce the overall resultant (e.g., four pump segments may each be out of phase with each other by approximately 90 degrees). Other pump segment configurations are also contemplated. In addition, the phase of the pulses may be adjusted based on the configuration and placement of the pump segments 103 (e.g., one pump segment may be longer than another pump segment). The cancellations may result in a pump system with lower amplitude pulsations. The additional pump segments may result in a higher net flow rate at a given hub-roller rotational speed.

FIG. 6 illustrates a chart of individual fluid flow profiles and a combined resultant flow profile, according to an embodiment. As seen in FIG. 6 pulsations 601a caused by pump 1 (e.g., pump segment 103a) may be out of phase with pulsations 601b caused by pump 2 (e.g., pump segment 103b). A pulse (e.g., pulse 609) in the flow profile may include a section of the flow profile between a respective peak (e.g., peak 605) and a respective valley (e.g., valley 607). The resultant 603 may be a flow profile with reduced pulsations.

In some embodiments, the geometry of the channel transition regions 115 and/or transition channels 157 may further reduce the pulsations in the flow profiles. The channel transition regions 115 may have internal cross-sections that taper up to the full cross-section of pump segments 103. These regions may reduce the abrupt change in displaced volume as rollers 201 transition on or off of pump segments 103. In some embodiments, the angular placement of the pump segments 103 may be configured to further reduce pulsations (e.g., different angular placements may be tested to determine which placement results in the smallest resultant pulsations for a given roller configuration). In some embodiments, the sheet 107 may be molded into other shapes to configure the pump segments 103 to reduce pulsations (e.g., see FIG. 9). In some embodiments, the placement of the rollers 201 may be calculated according to the number and size of the rollers 201, configuration of the pump segments 103, etc. to reduce the resultant pulse amplitudes. For example, the embodiment shown in FIG. 5a includes 7 rollers 201 which may be equally angularly spaced from each other as the two pump segments 103a,b are approximately symmetric. In some embodiments, the placement of the rollers 201 may be adjusted as needed to further reduce resultant pulse amplitudes (which may be detected, for example, during testing). For example, if roller 201a and roller 201n are slightly more angularly separated than roller 201c and roller 201d or if pump segment 103a is slightly longer than pump segment 103b, the resultant flow may include a larger pulse amplitude, as these rollers engage and disengage the pump segments 103, than if the rollers 201 and pump segments 103 were perfectly symmetric. Other irregularities in the pump segments and/or rollers may also result in pulses in the resultant. The placement of the rollers 201 may be adjusted to compensate for the pulses in the resultant (e.g., roller 201a and roller 201n may be brought closer together until the pulse amplitude in the resultant is reduced).

FIG. 7 illustrates an embodiment of a console 701 for using a cassette 100 with multiple pump segments 103. In some embodiments, the two or more pump segments 103 may be implemented on a cassette 100 received into cassette receiving portion 703 of console 701 to be used in phacoemulsification cataract surgery (other surgery types are also contemplated). The roller head 203/peristaltic pump motor 205 may be attached to the inside of the cassette receiving portion 703 in order to engage the rollers 201 with the pump segments 103 of the cassette 100 when the cassette 100 is received into the cassette receiving portion 703.

Figure 8:
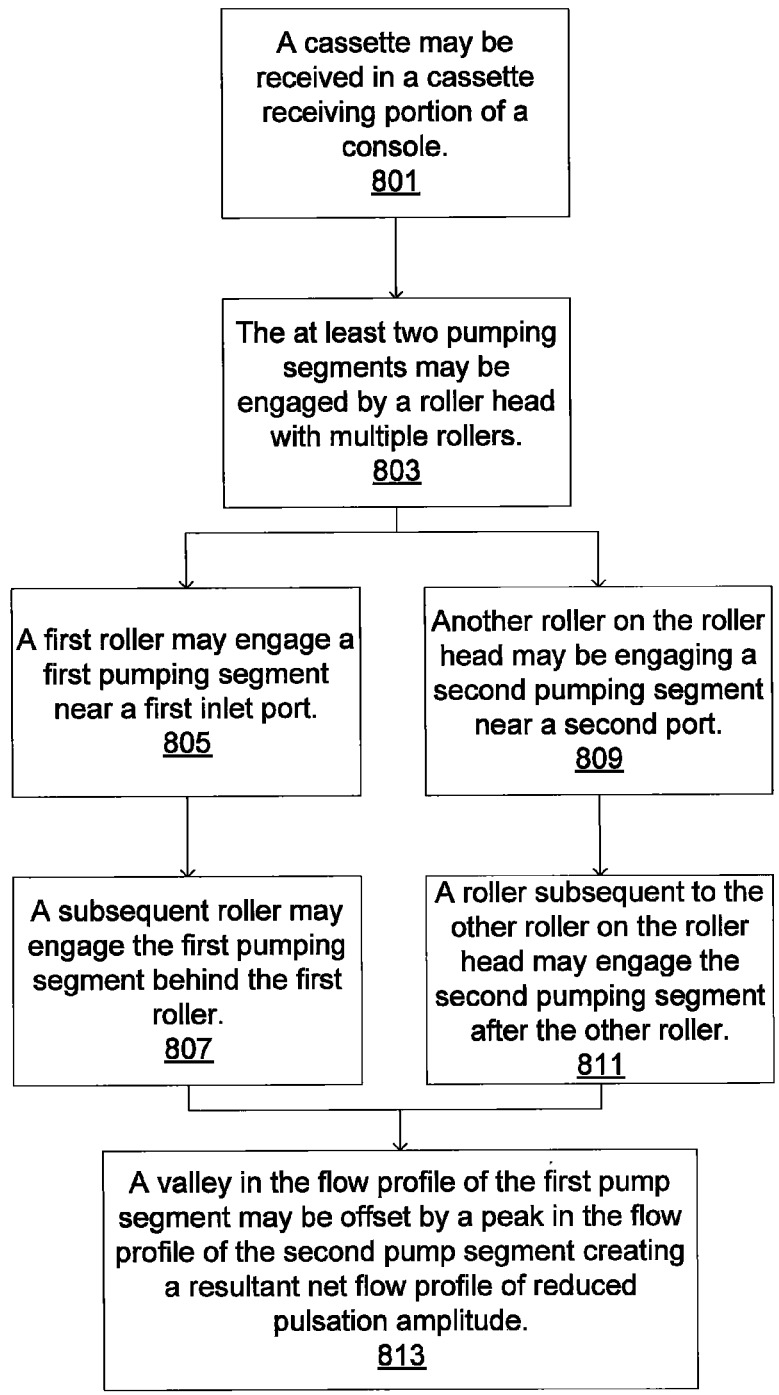
FIG. 8 illustrates an embodiment of a method for increasing pump flow and reducing pulsation amplitudes using multiple pump segments.

FIG. 8 illustrates an embodiment of a method for increasing pump flow and reducing pressure pulsations using multiple pump segments 103. The elements provided in the flowchart are illustrative only. Various provided elements may be omitted, additional elements may be added, and/or various elements may be performed in a different order than provided below.

At 801, a cassette 100 may be received in a cassette receiving portion 703 of a console 701. In some embodiments, the cassette 100 may include a sheet 107 and a substrate 105 coupled to the sheet 107 such that the sheet 107 and the substrate 105 form at least two pump segments 103.

At 803, the at least two pump segments 103 may be engaged by a roller head 203 with multiple rollers 201. The two or more pump segments 103 may produce additional flow (e.g., approximately twice the flow for two segments as opposed to one) than if the cassette had only one pump segment engaging the roller head.

At 805, roller 201c (as seen in FIGS. 5a-c) may engage pump segment 103a by first rolling over a transition region 115a with an underlying transition channel 157. As the roller 201c rolls off of the transition region 115a (and correspondingly, off of the transition channel 157), the roller 201c may form an internal seal within the pump segment 103a at point 161. The internal seal may move with the roller 201c through the "active" region 163. At this point, fluid 155 in front of the roller's motion may be pushed through the pumping channel 103a while fluid 155 behind the roller's motion may be pulled from the inlet (e.g., inlet 112a).

At 807, the next roller 201d on the roller head 203 may approach the transition region 115a/transition channel 157 behind the roller 201c that is currently forming an internal seal. Roller 201d may begin to reduce the cross sectional space between the sheet 107 underlying roller 201d and the substrate 105. As the cross sectional space is reduced, fluid 155 being pulled by roller 201c may slowly be constrained. The fluid flow from the inlet as a result of the sealed active roller may slowly be reduced by the transition roller until the transition roller (e.g., roller 201d) forms a new seal at the seal point 161 and becomes the new active roller (which may effectively isolate the front roller 201c which had previously formed a seal). The sequence may then be repeated as the next roller 201e in the sequence engages the start of the transition region 115a/transition channel 157.

At 809, as roller 201c was forming a seal at point 161, roller 201n may be starting to engage transition region 115d on pump segment 103b.

At 811, roller 201n and subsequent roller 201a may follow a similar sequence on pump segment 103b (e.g., with seal point 169) as rollers 201c and 201d followed at 805 and 807. Rollers 201n/201a may be 180 degrees out of sequence on pump segment 103b as rollers 201c/201d on pump segment 103a. In some embodiments, inlets 112a and 112c may be pulling fluid 155 from the same source (e.g., inlet 112a and inlet 112c may be fluidly coupled to the same aspiration line through port 509).

At 813, a valley in the flow profile caused by rollers 201 acting on pump segment 103a may be offset by a peak in the flow profile caused by rollers 201 acting on pump segment 103b to create a resultant net flow profile from ports 112a and 112c (which may be fluidly connected) of reduced pulsation amplitude (than a flow profile from either of the pump segments 103a,b individually). The positioning of the rollers 201 on the roller head 203 with respect to the pump segments 103 may be used to create offsetting pulses such that a pulse peak created in the fluid flow from inlet 112a may be offset by a corresponding pulse valley in fluid flow from inlet 112c resulting in a more constant resultant fluid flow/pressure from the source to inlet 112a and 112c (similarly, fluid flow to exhaust 112b and 112d may have offsetting pulses resulting in a more constant resultant fluid flow/pressure to the exhaust). In some embodiments, adjustments may be made to the pump segments 103 and/or rollers 201 to further reduce the pulsation amplitudes of the resultant flow. For example, the angular positioning of the various pump segments 103 relative to each other may be adjusted. As another example, the shapes of the pump segments 103 may be adjusted to further reduce pulsations. In some embodiments, the placement of the rollers 201 on the roller head 203 may be adjusted (e.g., the placement of rollers 201 on the roller head 203 may be adjusted to further reduce pulse amplitudes in the resultant flow).

As seen in FIG. 5a, cassette 100b may include additional elements that provide control of irrigation fluid as well as aspiration fluid. Upstream of port 509, cassette 100b may include a pressure sensor 513, which may be any of a variety of non-invasive pressure sensors such as those disclosed in U.S. Pat. No. 5,910,110 (Bastable) and U.S. Pat. No. 5,470, 312 (Zanger, et al.), the entire contents of both patents being incorporated herein by reference. Cassette 100b may also include a vent pinch valve site 515 for allowing the venting of any vacuum from pump segments 103. Irrigation fluid may enter cassette 100b through port 517 and may exit cassette 100b through port 519 and may be controlled by valve or pinch valve site 521, which may be actuated by a plunger. Vent 515 may be operated in a similar method. In addition, between port 517 and irrigation pinch valve site 521, cassette 100b may include an irrigation pressure interface 550. Pressure interface 550 may be made from a thin molded membrane contained within sheet 107 (which may extend to pressure interface 550) over a fluid chamber contained within substrate 105. Such an interface may allow detection of irrigation pressure in a non-invasive manner using a surface contact pressure transducer or calibrated load cell. In some embodiments, one or more of the pressure sensors (e.g., pressure sensor 513 and/or interface 550) may be located in a central location.

Various modifications may be made to the presented embodiments by a person of ordinary skill in the art. For example, although some of the embodiments are described above in connection with phacoemulsification cataract surgery it can also be used with other procedures using a peristaltic pump. Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A surgical cassette configured to engage a plurality of rollers of a peristaltic pump, comprising:
   at least one sheet; and
   at least one rigid substrate coupled to the at least one sheet; wherein the at least one sheet and the at least one substrate form at least two separate semi-circular pump segments such that fluid flowing through the at least two semi-circular pump segments contacts the at least one rigid substrate and the at least one sheet;
   wherein the at least two semi-circular pump segments are configured to engage the plurality of rollers of the peristaltic pump, wherein the at least two separate semi-circular pump segments align to overlap with a circular travel path of the plurality of rollers such that each roller of the plurality of rollers travels over each of the at least two semi-circular pump segments in a repeating, serial order; and
   wherein at least one of the at least two pump segments includes a transition region at an angular end and wherein the transition region has a tapered internal cross-section.

2. The surgical cassette of claim 1, wherein the at least two pump segments are configured to engage a single roller head of a peristaltic pump comprising the plurality of rollers.

3. The surgical cassette of claim 2, wherein at least one of the at least two pump segments is configured to provide a flow profile in which a peak of a pulse from the at least one pump segment is at least partially out of phase with a peak of a pulse from at least one other pump segment of the at least two pump segments when the at least two pump segments engage the single roller head.

4. The surgical cassette of claim 3, wherein the at least one of the at least two pump segments comprises a first pump segment and wherein the at least one other pump segment comprises a second pump segment and wherein respective peaks of the pulses provided through the first pump segment and the second pump segment are approximately 180 degrees out of phase.

5. The surgical cassette of claim 4, wherein the pulses provided by the first pump segment and the second pump segment are configured to be combined to form resultant pulses that have pulsation amplitudes that are smaller than pulsation amplitudes of the pulses provided by the first pump segment and smaller than pulsation amplitudes of the pulses provided by the second pump segment.

6. The surgical cassette of claim 1, wherein the at least one sheet includes an elastomeric sheet.

7. The surgical cassette of claim 1, wherein the at least two pump segments form separate fluid paths such that fluid entering one pump segment of the at least two pump segments does not enter any other pump segment of the at least two pump segments.

8. The surgical cassette of claim 1, wherein the at least one sheet is a single sheet and the at least one substrate is a single substrate such that all of the at least two pump segments are formed between the single sheet and the single substrate.

9. A system, comprising:
   a surgical cassette, comprising:
      at least one sheet; and
      at least one rigid substrate coupled to the at least one sheet; wherein the at least one sheet and the at least one substrate form at least two separate semi-circular pump segments such that fluid flowing through the at least two semi-circular pump segments contacts the at least one rigid substrate and the at least one sheet;
   a surgical console, comprising:
      a surgical cassette receiving portion configured to receive the cassette; and
      a roller head comprising a plurality of rollers configured to engage the at least two pump segments when the cassette is received in the cassette receiving portion;
   wherein the at least two separate semi-circular pump segments align to overlap with a circular travel path of the plurality of rollers such that each roller of the plurality of rollers travels over each of the at least two semi-circular pump segments in a repeating, serial order;
   wherein at least one of the at least two pump segments is configured to provide a flow profile in which a peak of a pulse from the pump segment is at least partially out of phase with a peak of a pulse from at least one other pump segment of the at least two pump segments when the at least two pump segments engage the single roller head,
   wherein at least one of the at least two pump segments includes a transition region at an angular end and wherein the transition region has a tapered internal cross-section.

10. The system of claim 9, wherein the at least one of the at least two pump segments comprises a first pump segment and wherein the at least one other pump segment comprises a second pump segment and wherein respective peaks of the pulses provided through the first pump segment and the second pump segment are approximately 180 degrees out of phase.

11. The system of claim 10, wherein the system is configured to combine the pulses provided by the first pump segment and the second pump segment to form a resultant flow that has pulsation amplitudes that are smaller than pulsation amplitudes of the pulses provided by the first pump segment and smaller than pulsation amplitudes of the pulses provided by the second pump segment.

12. The system of claim 9, wherein the at least two pump segments are configured to be angularly positioned relative to the roller head when the at least two pump segments engage the roller head.

13. The system of claim 9, wherein the at least one sheet includes an elastomeric sheet.

14. The system of claim 9, wherein the at least two pump segments form separate fluid paths such that fluid entering one pump segment of the at least two pump segments does not enter any other pump segment of the at least two pump segments.

15. A method, comprising:
receiving a cassette in a cassette receiving portion of a console, wherein the cassette comprises at least one sheet and at least one rigid substrate coupled to the at least one sheet such that the at least one sheet and the at least one substrate form at least two separate semi-circular pump segments wherein fluid flowing through the at least two pump segments contacts the at least one rigid substrate and the at least one sheet;
engaging the at least two pump segments with a roller head comprising a plurality of rollers, wherein the at least two separate semi-circular pump segments align to overlap with a circular travel path of the plurality of rollers such that each roller of the plurality of rollers travels over each of the at least two semi-circular pump segments in a repeating, serial order, wherein at least one of the at least two pump segments includes a transition region at an angular end and wherein the transition region has a tapered internal cross-section;
wherein at least one of the at least two pump segments is configured to provide a flow profile in which a peak of a pulse from the pump segment is at least partially out of phase with a peak of a pulse from at least one other pump segment of the at least two pump segments when the at least two pump segments engage the single roller head.

16. The method of claim 15, wherein the at least one of the at least two pump segments comprises a first pump segment and wherein the at least one other pump segment comprises a second pump segment and wherein respective peaks of the pulses provided through the first pump segment and the second pump segment are approximately 180 degrees out of phase.

17. The method of claim 16, further comprising combining the pulses provided by the first pump segment and the second pump segment to form a resultant flow that has pulsation amplitudes that are smaller than pulsation amplitudes of the pulses provided by the first pump segment and smaller than pulsation amplitudes of the pulses provided by the second pump segment.

18. The method of claim 15, wherein the at least two pump segments are configured to be angularly positioned relative to the roller head when the at least two pump segments engage the roller head.

19. The method of claim 15, wherein the at least one sheet includes an elastomeric sheet.

20. The method of claim 15, wherein the at least two pump segments form separate fluid paths such that fluid entering one pump segment of the at least two pump segments does not enter any other pump segment of the at least two pump segments.

* * * * *